(12) United States Patent
Rojo

(10) Patent No.: US 10,371,623 B2
(45) Date of Patent: Aug. 6, 2019

(54) CORROSION TEST CHAMBER

(71) Applicant: Nelson Rojo, Diadema (BR)

(72) Inventor: Nelson Rojo, Diadema (BR)

( * ) Notice: Subject to any disclaimer, the term of this patent is extended or adjusted under 35 U.S.C. 154(b) by 297 days.

(21) Appl. No.: 14/998,714

(22) Filed: Feb. 5, 2016

(65) Prior Publication Data

US 2017/0227449 A1    Aug. 10, 2017

(51) Int. Cl.
  *G01N 17/00*    (2006.01)
  *F28D 1/06*    (2006.01)

(52) U.S. Cl.
  CPC ............. *G01N 17/002* (2013.01); *F28D 1/06* (2013.01)

(58) Field of Classification Search
  CPC ...................................................... C12M 41/14
  See application file for complete search history.

(56) References Cited

U.S. PATENT DOCUMENTS

| | | | |
|---|---|---|---|
| 2,274,541 A | 2/1942 | Fontana et al. | |
| 2,405,532 A | 8/1946 | Todd | |
| 2,521,921 A | 9/1950 | Kolar, Jr. | |
| 2,766,624 A | 1/1954 | Heffner | |
| 2,669,895 A | 2/1954 | Leis | |
| 2,897,060 A | 7/1959 | Dleman | |
| 2,957,972 A | 12/1960 | Seidman | |
| 3,131,029 A | 4/1964 | Dieman | |
| 3,162,497 A | 12/1964 | Boswinkle et al. | |
| 3,488,681 A | 1/1970 | Ikuo Mita et al. | |
| 3,542,517 A | 11/1970 | Gill | |
| 3,886,791 A | 6/1975 | Grossman | |
| 4,069,019 A | 1/1978 | Suga | |
| 4,114,813 A | 9/1978 | Suga | |
| 4,357,499 A | 11/1982 | Bruel | |
| 4,361,620 A | 11/1982 | Newton | |
| 4,455,246 A * | 6/1984 | Schmidt ................. | C04B 14/06 106/636 |
| 4,667,522 A | 5/1987 | Kawahara | |
| 4,770,031 A | 9/1988 | Roth et al. | |
| 5,380,981 A | 1/1995 | Feldman et al. | |
| 5,454,428 A | 10/1995 | Pickard et al. | |
| 5,529,716 A | 6/1996 | Nomura et al. | |
| 5,741,579 A | 4/1998 | Nishizawa | |
| 6,046,907 A | 4/2000 | Yamaguchi | |
| 6,108,489 A | 8/2000 | Frohlich et al. | |
| 6,215,110 B1 | 4/2001 | Jones | |
| 6,220,523 B1 | 4/2001 | Fiedrich | |
| 6,337,121 B1 | 1/2002 | Majalahti | |
| 6,794,030 B1 | 9/2004 | Okada et al. | |
| 7,021,372 B2 | 4/2006 | Pickard et al. | |
| 7,320,245 B2 | 1/2008 | Jaralla | |

(Continued)

OTHER PUBLICATIONS

Interplastic Corporation, http://www.interplastic.com/p-corrosion_bisphenol.php, obtained using Wayback Machine from Feb. 8, 2014 Year: 2014).*

*Primary Examiner* — Matthew D Krcha

(74) *Attorney, Agent, or Firm* — Thomas Grzesik; Fleit Gibbons Gutman Bongini & Bianco P.L.

(57) ABSTRACT

A multilayer temperature control shell for a test chamber to control the temperature within the interior of the test chamber wherein the multilayer temperature control shell comprises an inner temperature generating zone and an outer temperature insulating zone disposed between an interior layer of sealant and an exterior layer of sealant.

16 Claims, 4 Drawing Sheets

(56) References Cited

U.S. PATENT DOCUMENTS

| | | |
|---|---|---|
| 8,288,689 B1 | 10/2012 | Adelman |
| 8,342,046 B2 | 1/2013 | Murakami et al. |
| 8,723,535 B2 | 5/2014 | Zhang et al. |
| 8,888,978 B2 | 11/2014 | Mitchell et al. |
| 8,951,802 B2 | 2/2015 | Bridenbaker |
| 2006/0057713 A1* | 3/2006 | Cecchi .................. C12M 23/48 435/303.1 |
| 2010/0218912 A1* | 9/2010 | Lawless ................ C09K 8/467 165/45 |
| 2011/0315783 A1* | 12/2011 | Baker ...................... B01L 7/52 236/3 |
| 2015/0047807 A1 | 2/2015 | Fiedrich |
| 2015/0184055 A1 | 7/2015 | Raman et al. |

\* cited by examiner

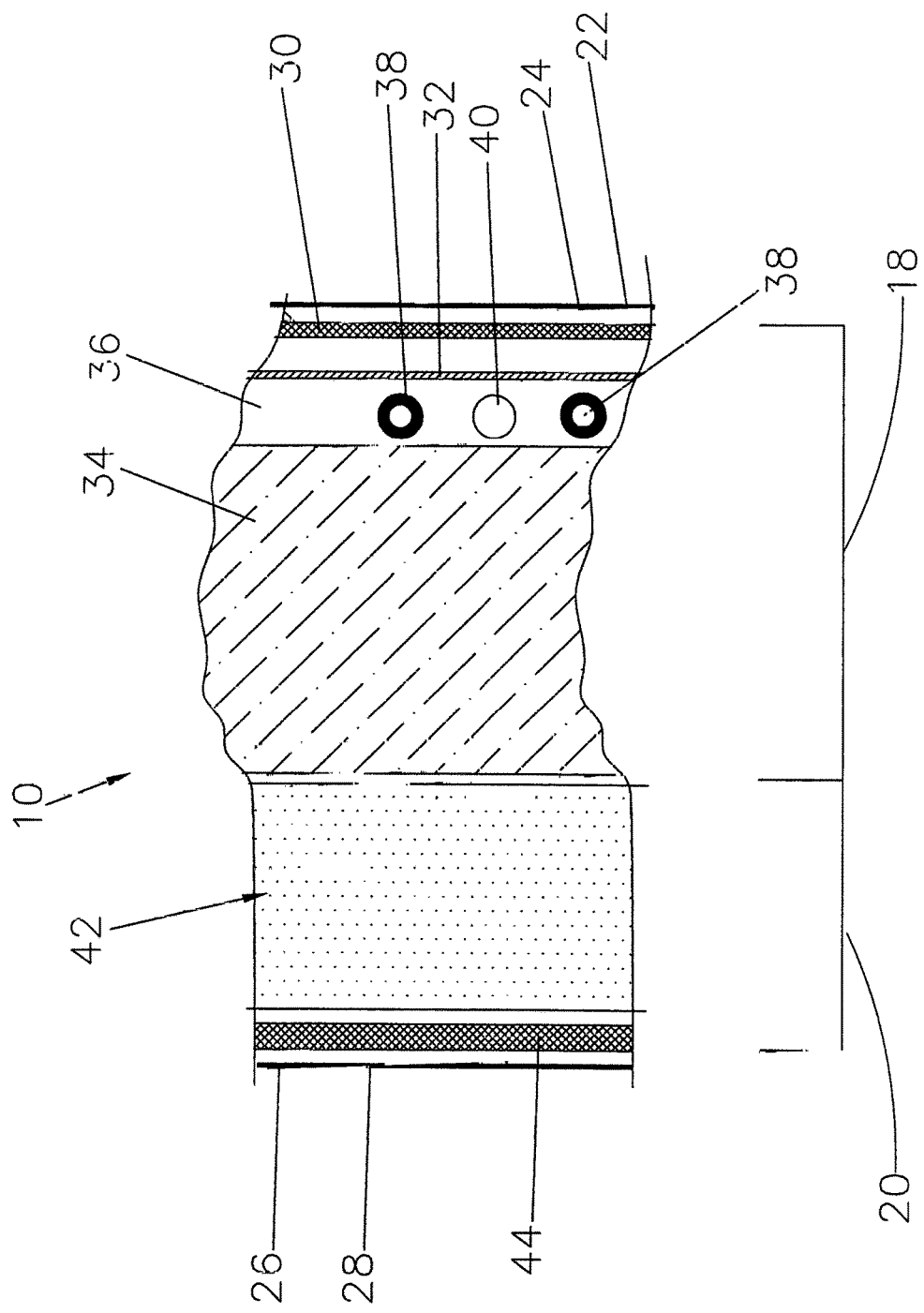

CORROSION TEST CHAMBER

BACKGROUND OF THE INVENTION

Field of the Invention

A multilayer temperature control shell for a corrosion test chamber to control the temperature within the interior of the corrosion test chamber.

Description of the Prior Art

Various specimens or workpieces are exposed to accelerated corrosion conditions controlled test chambers to determine the effective life span or duration of utility of such products. These tests commonly include testing with water or a saline solution to simulate a salt load such as when salt is applied to a roadway to treat snow and ice conditions during winter weather and/or acids. In addition, temperature may be varied within the test chamber as well as predetermined or variable relative humidity and/or a predetermined or variable salinity content to test the specimens. A controller is generally connected to a heater, fluid source such as water saline solution, oil or air and one or more temperature and humidity sensors disposed within the test chamber in order to control internal environment of the test chamber.

U.S. Pat. No. 8,951,802 describes a test chamber typical of the prior art.

More pertinent to the instant invention a number of prior art documents are directed to various heat transfer/insulation techniques are disclosed in the following references.

U.S. Pat. No. 6,046,907 shows a heat conductor disposed between a heat sink and electronic parts mounted on a printed circuit board. The heat conductor is layered by a heat conductive layer, made of silicone gel with alumina as a heat conductive filler dispersed therein and an adhesive layer. The adhesive layer consists of a hot melt layer, with alumina as a heat conductive filler dispersed therein, and a heat resistant film, to facilitate formation of the hot melt layer, adhered to the heat conductive layer on one face of the heat resistant film.

U.S. Pat. No. 5,529,716 describes a liquid crystal polyester resin composition comprising a liquid crystal polyester, aluminum powders, flakes and/or fibers, and titanium oxide and/or talc.

U.S. Pat. No. 4,361,620 relates to a heat energy exchange medium incorporated in an energy exchange device for transferring heat and moisture between two airstreams in an air supply system. The exchange medium is aluminum having a coating of hydrated calcium and aluminum oxides or hydroxides to render its heat transfer surfaces capable of exchanging latent as well as sensible heat energy. The aluminum forms a conversion coating portion comprising an hydrated calcium aluminate next to the aluminum surface which, in turn, secures the insoluble gel-like precipitate coating portion of hydrated calcium and aluminum oxides or hydroxides thereto.

U.S. Pat. No. 6,337,121 relates to a sound proofing and heat insulation mat comprising a sheet of insulation material, a thin aluminum foil mounted on the insulation sheet and a thin metal sheet layer covering pipes.

U.S. Pat. No. 5,741,579 shows a heat-conductive sheet used for the transfer of heat from a heat generating device to heat a sink member mounted thereon by intervening therebetween. The heat-conductive sheet is a laminar body comprising an aluminum foil and a layer of a gel-like composite material consisting of a cured organopolysiloxane as the matrix phase and inorganic heat-conductive particles as the dispersed phase in the matrix.

U.S. Pat. No. 5,380,981 relates to an electric heating unit attached to the rear surface of a mirror to reduce the formation of condensation on the mirror surface including a moisture resistant low heat conductivity heat barrier formed of a layer of closed cell plastic foam, a length of insulated low resistance heater wire mounted on the surface of the foam layer and connected to a voltage source, an aluminum foil covering the heater wire and the surface of the foam layer and adhesively connected thereto, an adhesive layer covering the outer surface of the aluminum foil, and a peel-off backing covering the adhesive layer to permit attachment of the heater unit to a mirror when backing is removed.

U.S. Pat. No. 2,957,972 relates to a salt spray test chamber comprises a floor element, plurality of side wall elements and a roof or lid element, pivotal means including a pair of hydraulic cylinders and for opening the lid and side doors. The elements are arranged to form an enclosed chamber the interior of which supports one or more spray nozzles which form a continuous fog that contacts the exposed surface of the articles being tested.

The outer shell may be formed of sheet synthetic resinous material or sheet metallic material, a relatively thick insulative lining, of fiberglass or similar material contacts the inner surface of the external shell. The inner surface of the lining is covered by an electrically conductive heating/cooling blanket. The inner layer of the blanket is coated with an adhesive layer upon which, in turn, a lining of non-corrosive steel is placed. A second protective layer of inert synthetic resinous material may be used as a final layer.

U.S. Pat. No. 8,342,046 discloses a second tank to accommodate a sample to be tested disposed within a first tank. A heat conducting member is disposed such that one end of the heat conducting member is positioned in the gas inside the first or second tank and the other end is positioned in the humidifying water contained in the humidifier. The heat conducting member is made of material having higher thermal conductivity than that of gas inside the first or second tank.

U.S. Pat. No. 4,667,522 describes a humidity testing apparatus comprising a test chamber with external heaters for superheating steam and preventing condensation in the testing zone. The test chamber is divided into an upper humidity testing section and lower condensate collection and removal section by a horizontal heating plate extending from the back wall to a front edge adjacent to and spaced apart from the front of the test chamber, the heating plate extending from one sidewall to the opposing sidewall of the chamber.

U.S. Pat. No. 3,886,791 shows an apparatus for simulating the effects of extended outdoor weathering on paint, plastics, textiles, and other surfaces and samples including the effects of light, humidity, condensation, heat and/or atmospheric pollutants. The apparatus includes a closed chamber, sample holders inside the chamber and around the outside wall and partially isolating the space between the sample and the outside wall to maintain the temperature therein below, but close to, the chamber interior temperature and above the ambient temperature outside the wall while having what is functionally the same moisture and pollutant content throughout the chamber, including the partially isolated space.

U.S. Pat. No. 5,454,428 relates to a thermally conductive filler and resin composition including metallic powders or flakes of aluminum, copper, bronze or brass and fiberous material added to the resin composition to provide a thermally conductive resin.

US 2010/0218912 discloses a method of subterranean ground heat exchange comprising the steps of flowing a fluid medium through an underground casing such that thermal energy is conducted through a wall of the casing. The wall of the wall is a composite wall formed from a thermosetting plastic composition and a reinforcing fiber material wherein: (a) the reinforcing fiber material is fiberglass, carbon fiber, or a combination thereof: (b) the thermosetting plastic composition from which the composite wall is formed includes an amount of a thermal conductivity enhancing additive is aluminum flake, aluminum powder, aluminum oxide, aluminum nitrate, silicone carbide, Raney nickel, silver-coated copper, or a combination thereof.

U.S. Pat. No. 6,794,030 relates to a heat conductive sheet including a substrate and a heat conductive resin layer applied to at least one surface of the substrate wherein the heat conductive resin layer contains a binder resin and a heat conductive filler dispersed in the binder resin.

Additional examples of the prior art are found in the following documents: U.S. Pat. Nos. 2,274,541; 2,405,532; 2,521,921; 2,669,865; 2,766,624; 2,897,060; 3,131,029; 3,163,497; 3,488,681; 3,542,517; 4,069,019; 4,114,813; 4,357,499; 4,770,031; 6,108,489; 6,215,110; 6,220,523; 7,021,372; 7,320,245; 8,288,689; 8,723,535; 8,888,976; US 2015/0047807 and US 2015/0184055.

While various elements, in part, similar to some components of the instant invention are known, the combination of structural elements are neither thought nor suggested.

SUMMARY OF THE INVENTION

The present invention relates to a multilayer temperature control shell for a test chamber to control the temperature within the interior of the test chamber.

The test chamber comprises the multilayer temperature control shell having a cover or lid hingedly coupled thereto to enclose the interior of the test chamber when the cover or lid is closed. Test specimens or work pieces are placed in the interior of the test chamber where the test specimens or work pieces are exposed to mist, humidity, acids, saline solutions or other deleterious environmental conditions through a spray manifold or nozzles.

The multilayer temperature control shell comprises an inner temperature generating zone and an outer temperature insulating zone disposed between an interior layer of sealant and an exterior layer of sealant.

The inner temperature generating zone comprises an interior layer of temperature conductive material, and a layer of temperature distribution material and layer of insulation material disposed in spaced relationship relative to each other to receive a plurality of heating elements and a plurality of cooling elements.

The layer of temperature distribution material may comprise a sheet or film of temperature conductive material.

The interior layer of temperature conductive material may comprise a fibrous material impregnated with temperature conductive material.

The outer temperature insulating zone comprises fluid jacket of gas or liquid formed between the layer of insulation material of the inner temperature generating zone and an exterior layer of temperature insulation material.

The heating elements may comprise a silicone heater, a continuous element of resistive wire or individual strands of resistive wire coupled to a power source to selectively heat the space or gap formed between the layer of temperature distribution material and the layer of insulation material.

The cooling elements may comprise a continuous cooling coil or individual cooling elements coupled to a refrigerated system to selectively cool the space or gap formed between the layer of temperature distribution material and the layer of insulation material.

Whether heating or cooling, the energy is transferred to the interior of the test chamber by conduction through the interior layer of temperature conductive material.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 4 is an exploded cross-sectional view of the multilayer temperature control shell of the present invention taken along line 3-3 of FIG. 2.

Similar reference characters refer to similar parts throughout the several views of the drawings.

DETAILED DESCRIPTION OF THE INVENTION

Figure 1:
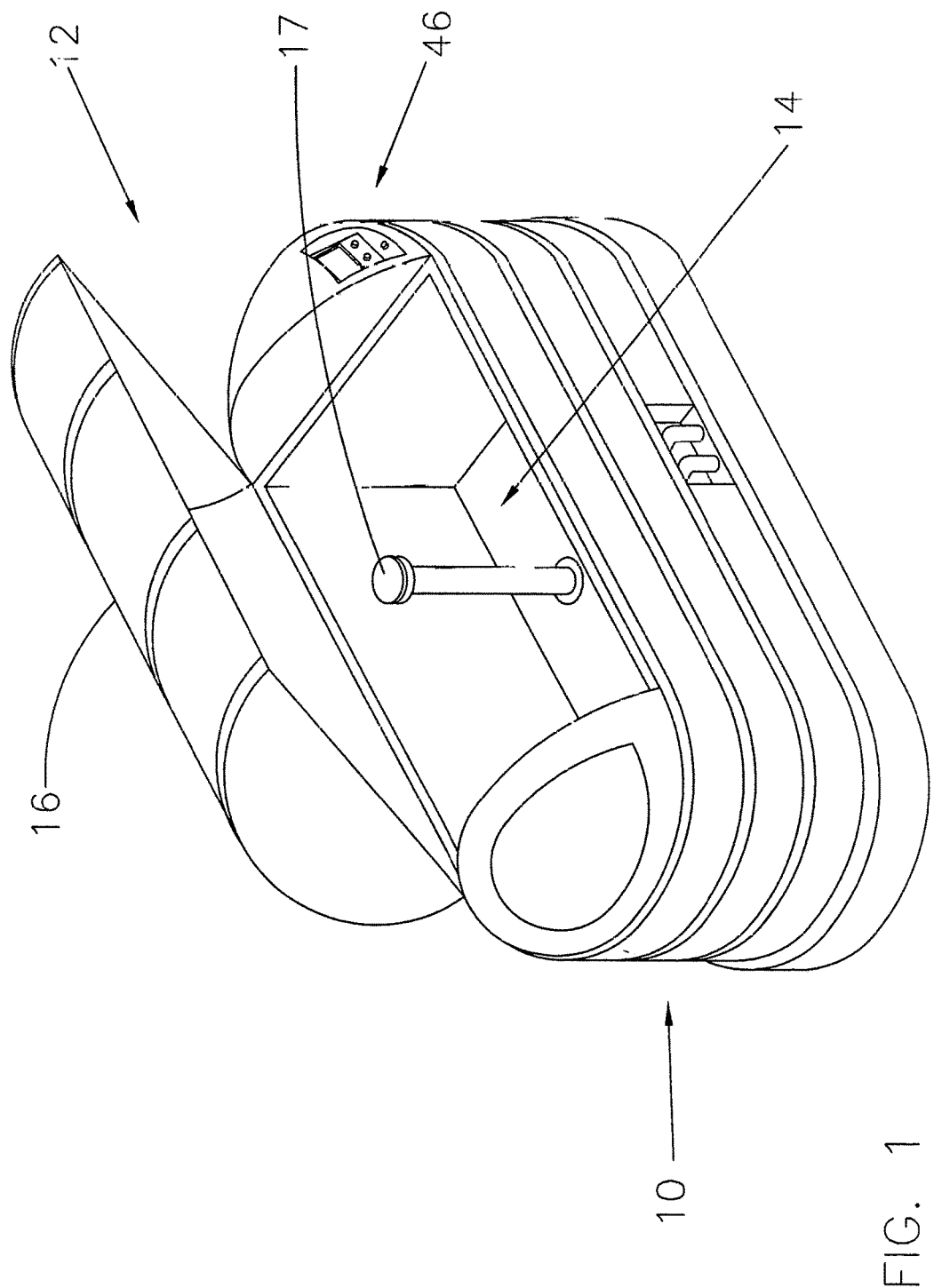
FIG. 1 is a perspective view of a test chamber including the multilayer temperature control shell of the present invention.
Figure 2:
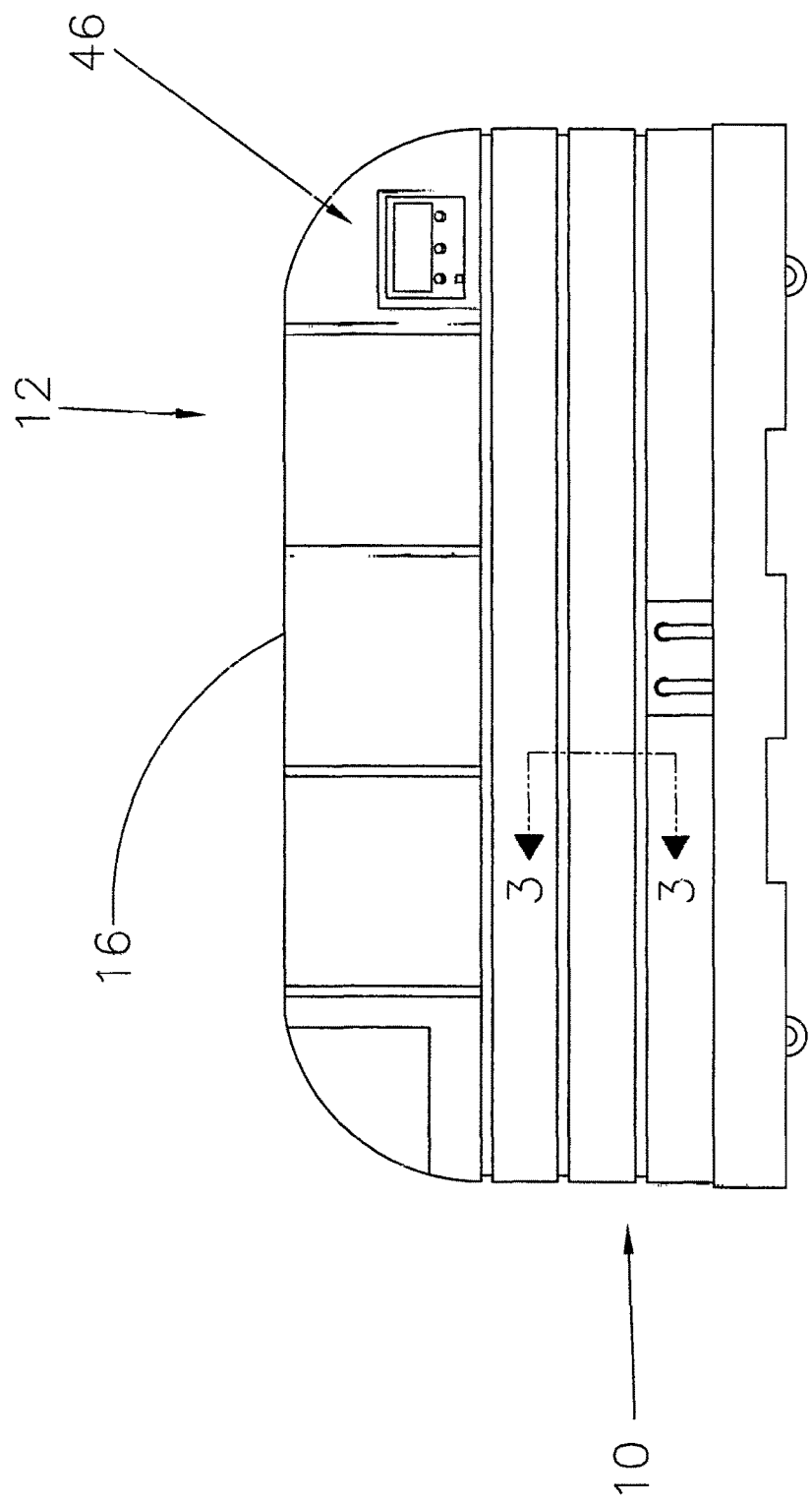
FIG. 2 is a front view of a test chamber including the multilayer temperature control shell of the present invention.

As shown in FIGS. 1 through 4, the present invention relates to a multilayer temperature control shell generally indicated as 10 for a test chamber generally indicated as 12 to control the temperature within the interior 14 of the test chamber 12. The multilayer temperature control shell 10 includes a layer of resin impregnated with a metallic powder or particles to increase the temperature coefficient of the multilayer temperature control shell 10.

The test chamber 12 comprises the multilayer temperature control shell 10 having a cover or lid 16 hingedly coupled thereto to form a cavity within the interior 14 of the test chamber 12 when the cover or lid 16 is closed. Test specimens or work pieces (not shown) are placed into the interior 14 of the test chamber 12 where the test specimens or work pieces (not shown) are exposed to mist, humidity, acids, saline solutions or other deleterious environmental conditions often through a spray manifold or nozzle 17.

Figure 3:
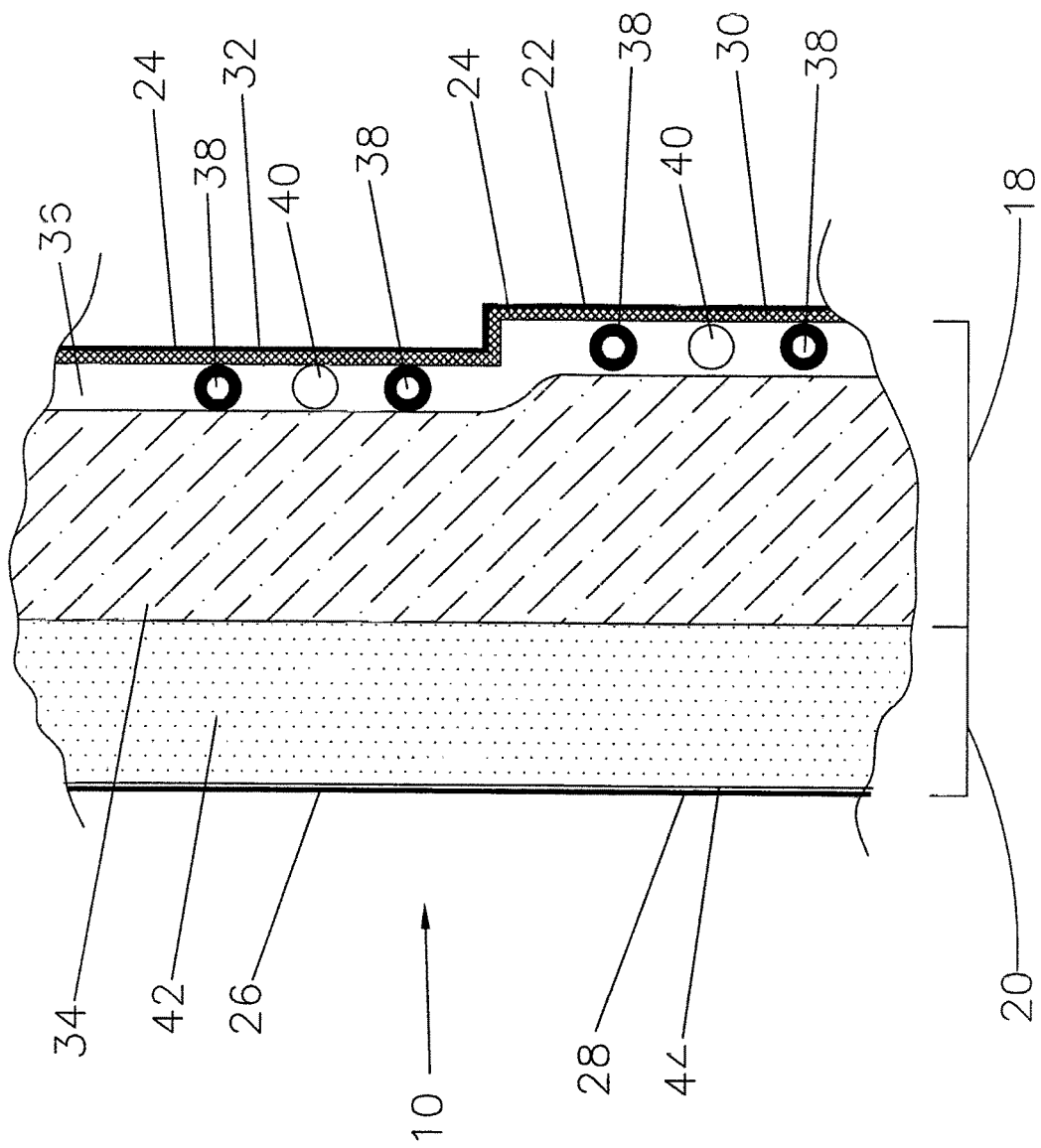
FIG. 3 is a cross-sectional view of the multilayer temperature control shell of the present invention taken along line 3-3 of FIG. 2.

As shown in FIGS. 3 and 4, the multilayer temperature control shell 10 comprises an inner temperature generating zone generally indicated as 18 and an outer temperature insulating zone generally indicated as 20 disposed between an interior layer of sealant 22 forming the interior surface 24 of the test chamber 12 and an exterior layer of sealant 26 forming the exterior surface 28 of the test chamber 12.

The inner temperature generating zone 18 comprises a interior layer of temperature conductive material 30, a layer of temperature distribution material 32 disposed adjacent to the interior layer of temperature conductive material 30 and an interior layer of insulation material 34 disposed adjacent to the outer temperature insulating zone 20. The layer of temperature distribution material 32 and the interior layer of insulation material 34 are disposed in spaced relationship relative to each other to cooperatively form a space or gap 36 therebetween to receive a plurality of heating elements each indicated as 38 and a plurality of cooling elements each indicated as 40. The outer surface or exterior of the interior layer of insulation material 34 is coated with resin to form a fluid proof barrier.

The interior layer of temperature conductive material 30 may comprise a fibrous material such as fiber glass impregnated with a mixture of at least about 75% bisphenol epoxy vinyl ester resin and from about 4% to about 20% temperature conductive metallic powder all by weight applied in a thickness of from about 5 mm to about 8 mm. The metallic powder may comprise aluminum DIN 100 (granulometry), copper DIN 100 (granulometry) or other metal with high thermal coefficient. Alternatively, the temperature conductive material may comprise temperature conductive particles such as aluminum, copper or other suitable metals.

The layer of temperature distribution material 32 may comprise a sheet or film of aluminum, copper or other heat conductive material ranging in thickness from about 0.5 mm to about 0.8 mm.

The layer of insulation material 34 may comprise an aluminized mineral fiber about 3 inches thick.

The outer temperature insulating zone 20 comprises a fluid jacket 42 about 50 mm wide formed between the inner layer of insulation material 34 of the inner temperature generating zone 18 and an exterior layer of insulation material 44 ranging in thickness from about 25 mm to about 50 mm and the exterior layer of sealant 26.

The interior layer of sealant 22 forming the interior surface 24 of the test chamber 12 and the exterior layer of sealant 26 form the exterior surface 28 of the test chamber 12 may comprise a gel-like coating such as bisphenol epoxy vinyl ester resin applied in a thickness of from shout 500 μm to about 1 mm.

The heating elements 38 may comprise individual silicone heating elements, a continuous element of resistive wire or conductor, individual strands of resistive wire or conductor coupled to a power source (not shown) to selectively heat the space or gap 36 formed between the layer of temperature distribution material 32 and the interior layer of insulation material 34. The cooling element 40 may comprise a continuous serpentine cooling coil or individual cooling elements coupled to a refrigeration system (not shown) to selectively cool the space or gap 36 formed between the layer of temperature distribution material 32 and the interior layer of insulation material 34.

Whether heating or cooling, the energy is distributed over the layer of temperature distribution material 32 and transferred to the interior 14 of the test chamber 12 by conduction through the interior layer of temperature conductive material 30.

The operation of the test chamber 12 is controlled through a control panel 46 employing existing state of the art sensors and control logic.

An alternate embodiment of the present invention comprises a multilayer temperature control liner for the test chamber 12 to control the temperature within the interior 14 of the test chamber 12.

The test chamber 12 comprises an outer shell 10 having a cover or lid 16 hingedly coupled thereto to form a cavity within the interior 14 of the test chamber 12 when the cover or lid 16 is closed. Test specimens or work pieces (not shown) are placed into the interior 14 of the test chamber 12 where the test specimens or work pieces (not shown) are exposed to mist, humidity, acids, saline solutions or other deleterious environmental conditions often through a spray manifold or nozzle 17.

As shown in FIGS. 3 and 4, the multilayer temperature control liner or inner temperature generating zone 18 is disposed between the interior layer of sealant 22 forming the interior surface 24 of the test chamber 12 and the outer shell 10.

The inner temperature generating zone 18 comprises the interior layer of temperature conductive material 30, the layer of temperature distribution material 32 disposed adjacent to the interior layer of temperature conductive material 30 and an interior layer of insulation material 34 disposed adjacent to the outer shell 10. The layer of temperature distribution material 32 and the interior layer of insulation material 34 are disposed in spaced relationship relative to each other to cooperatively form a space or gap 36 therebetween to receive a plurality of heating elements each indicated as 38 and a plurality of cooling elements each indicated as 40. The outer surface or exterior of the interior layer of insulation material is coated with resin to form a fluid proof barrier.

The interior layer of temperature conductive material 30 may comprise a fibrous material such as fiber glass impregnated with a mixture of at least about 75% bisphenol epoxy vinyl ester resin and from about 4% to about 20% temperature conductive metallic powder all by weight applied in a thickness of from about 5 mm to about 8 mm. The metallic powder may comprise aluminum DIN 100 (granulometry), copper DIN 100 (granulometry) or other metal with high thermal coefficient. Alternatively, the temperature conductive material may comprise temperature conductive particles such as aluminum, copper or other suitable metals.

The layer of temperature distribution material 32 may comprise a sheet or film of aluminum, copper or other heat conductive material ranging in thickness from about 0.5 mm to about 0.8 mm.

The layer of insulation material 34 may comprise an aluminized mineral fiber about 3 inches thick.

The outer shell 10 comprises a fluid jacket 42 about 50 mm wide formed between the inner layer of insulation material 34 of the inner temperature generating zone 18 and an exterior layer of insulation material 44 ranging in thickness from about 25 mm to about 50 mm and the exterior layer of sealant 26.

The interior layer of sealant 22 forming the interior surface 24 of the test chamber 12 and the exterior layer of sealant 26 form the exterior surface 28 of the test chamber 12 may comprise a gel-like coating such as bisphenol epoxy vinyl ester resin applied in a thickness of from about 500 μm to about 1 mm.

The heating elements 38 may comprise individual silicone heating elements, a continuous element of resistive wire or conductor, individual strands of resistive wire or conductor coupled to a power source (not shown) to selectively heat the space or gap 36 formed between the layer of temperature distribution material 32 and the interior layer of insulation material 34. The cooling element 40 may comprise a continuous serpentine cooling coil or individual cooling elements coupled to a refrigeration system (not shown) to selectively cool the space or gap 36 formed between the layer of temperature distribution material 32 and the interior layer of insulation material 34.

To assemble the test chamber 12, the multilayer temperature control liner 18 is placed inside the outer shell 10 and capped around the upper portion or periphery forming the fluid jacket 42 between the interior layer of insulation material 34 and the exterior layer of insulation material 44.

Whether heating or cooling, the energy is distributed over the layer of temperature distribution material 32 and transferred to the interior 14 of the test chamber 12 by conduction through the interior layer of temperature conductive material 30.

The method for producing the multilayer temperature control liner to control the temperature within the interior of the test chamber comprising the steps of:
fabricating a mold configured in the shape of the test chamber,
polishing the exterior of the mold,
applying a layer of resin or sealant to the exterior of the mold,
allowing the layer of resin or sealant to dry,
applying a layer temperature conductive fibrous material to the layer of resin or sealant,
allowing the layer of temperature conductive fiberous material to dry,
affixing a layer of temperature conductive film to the layer of temperature conductive fibrous material with resin,
allowing the resin used to affix the layer of temperature conductive material to the layer of temperature conductive fiberous material,
securing heating elements and cooling coils to the layer of temperature conductive material,
securing or applying a layer of insulation material to the outside of the heating elements and the cooling coils, and
applying a layer of resin or sealant to the exterior or outside surface of the layer of insulation.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A test chamber comprising:
a multilayer temperature control shell, the multilayer temperature control shell increasing an efficiency of temperature transfer to an interior of the test chamber and controlling temperature within the interior of the test chamber,
wherein the multilayer temperature control shell comprises
an inner temperature generating zone and an outer temperature insulating zone disposed between an interior layer of sealant and an exterior layer of sealant, wherein the inner temperature generating zone comprises an interior layer of temperature conductive material, where a first portion of the interior layer of temperature conductive material disposed in contact with a layer of temperature distribution material, and where a second portion of the interior layer of temperature conductive material is disposed in contact with the interior layer of sealant forming a wall defining at least a portion of the interior of the test chamber, and
wherein the interior layer of temperature conductive material comprises fiber glass impregnated with a mixture of resin and temperature conductive metallic powder.

2. The test chamber of claim 1, wherein the inner temperature generating zone further comprises an interior layer of insulation material disposed adjacent to the outer temperature insulating zone.

3. The test chamber of claim 2, wherein the layer of temperature distribution material and the interior layer of insulation material are disposed in spaced relationship relative to each other to cooperatively form a space of gap there between to receive one or more of at least one heating element and/or at least one cooling element.

4. The test chamber of claim 2, wherein the interior layer of insulation material comprises an aluminized mineral fiber.

5. The test chamber of claim 2, wherein the layer of temperature distribution material comprises a sheet or film of aluminum, copper or other heat conductive material.

6. The test chamber of claim 5, wherein the interior layer of insulation material comprises an aluminized mineral fiber.

7. The test chamber of claim 2, wherein the interior layer of insulation material is disposed in between one or more temperature altering elements and a fluid jacket.

8. The test chamber of claim 2, wherein the outer temperature insulating zone comprises a fluid jacket formed between the interior layer of insulation material of the inner temperature generating zone and an exterior layer of insulation material.

9. The test chamber of claim 1, wherein the layer of temperature distribution material comprises a sheet or film of aluminum, copper or other heat conductive material.

10. The test chamber of claim 1, wherein the interior layer of sealant forming an interior surface of the test chamber and the exterior layer of sealant forming an exterior surface of the test chamber comprise a gel-like coating.

11. The test chamber of claim 1, wherein the inner temperature generating zone further comprises an interior layer of insulation material disposed adjacent to the outer temperature insulating zone, the layer of temperature distribution material and the interior layer of insulation material are disposed in spaced relationship relative to each other to cooperatively form a space of gap there between to receive one or more of at least one heating element and/or at least one cooling element, and the outer temperature insulating zone comprises a fluid jacket formed between the interior layer of insulation material of the inner temperature generating zone and an exterior layer of insulation material.

12. The test chamber of claim 2, wherein the layer of temperature distribution material comprises a sheet or film of aluminum, copper or other heat conductive material, and the interior layer of insulation material comprises an aluminized mineral fiber.

13. A multilayer temperature control liner for a test chamber, the multilayer temperature control liner comprising:
an exterior surface;
an interior surface comprised of a sealant layer defining a cavity of the test chamber;
a layer of temperature conductive material disposed in contact with the interior surface and further disposed between the exterior surface and the interior surface, the layer of temperature conductive material comprising fiberglass impregnated with a mixture of resin and temperature conductive metallic powder, wherein the temperature conductive metallic powder increases a temperature coefficient of the multilayer temperature control liner, and wherein the layer of temperature conductive material is insulated from exposure to the cavity of the test chamber by the sealant layer, where the sealant layer contacts the layer of temperature conductive material; and an interior layer of insulation material disposed in spaced relationship with a layer of temperature distribution material cooperatively forming a space or gap there between, wherein one or more of at least one heating element and/or at least one cooling element is disposed within the space or gap.

14. The multilayer temperature control liner of claim 13, wherein the layer of temperature distribution material is disposed in contact with the layer of temperature conductive material.

15. The multilayer temperature control liner of claim 13, wherein the conductive metallic powder comprises aluminum.

16. A test chamber comprising:
a multilayer temperature control shell, wherein the multilayer temperature control shell comprises
an exterior surface;
an interior surface comprised of a sealant layer defining a cavity of the test chamber;
a first insulation layer comprising a first portion disposed in contact with the exterior surface;
a fluid jacket disposed comprising a first portion disposed in contact with a second portion of the first insulation layer;
a second insulation layer comprising a first portion disposed in contact with a second portion of the fluid jacket;
a plurality of temperature altering elements comprising a first portion disposed in contact with the second insulation layer;
a temperature distribution layer comprising a first portion disposed in contact with a second portion of the plurality of temperature altering elements; and
a temperature conductive layer comprising a first portion in contact with a second portion of the temperature distribution layer, and a second portion in contact with the sealant layer,
wherein the temperature conductive material comprises fiber glass impregnated with a mixture of resin and temperature conductive metallic powder.

* * * * *